(12) United States Patent
Neftel

(10) Patent No.: US 10,973,976 B2
(45) Date of Patent: *Apr. 13, 2021

(54) CONTROL DEVICE WITH RECOMMENDATIONS

(71) Applicant: Debiotech S.A., Lausanne (CH)

(72) Inventor: Frédéric Neftel, Crans-Montana (CH)

(73) Assignee: Debiotech S.A., Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/503,506

(22) Filed: Jul. 4, 2019

(65) Prior Publication Data

US 2019/0378604 A1    Dec. 12, 2019

Related U.S. Application Data

(63) Continuation of application No. 15/114,423, filed as application No. PCT/IB2015/050646 on Jan. 28, 2015, now Pat. No. 10,387,623.

(30) Foreign Application Priority Data

Jan. 28, 2014 (EP) .................................... 14152955
Jan. 29, 2014 (FR) .................................... 1450706

(51) Int. Cl.
*G05D 7/00* (2006.01)
*A61M 5/142* (2006.01)
(Continued)

(52) U.S. Cl.
CPC ........ *A61M 5/14244* (2013.01); *A61M 5/142* (2013.01); *A61M 5/1723* (2013.01); *G05B 15/02* (2013.01); *G16H 20/17* (2018.01); *G16H 40/63* (2018.01); *A61M 2205/502* (2013.01); *A61M 2205/505* (2013.01); *A61M 2230/201* (2013.01); *A61M 2230/63* (2013.01)

(58) Field of Classification Search
CPC ....... G16H 20/17; G16H 40/63; A61M 5/142; A61M 5/14244; A61M 5/1723; A61M 2205/505; A61M 2230/201; A61M 2230/63; A61M 2205/502; G05B 15/02
See application file for complete search history.

(56) References Cited

U.S. PATENT DOCUMENTS 5,609,575 A * 3/1997 Larson ................... G16H 20/17
                                                                  604/65
5,665,065 A     9/1997 Colman
(Continued)

FOREIGN PATENT DOCUMENTS

JP      2002-175372      6/2002
JP      2002-531884      9/2002
(Continued)

OTHER PUBLICATIONS

International Preliminary Report on Patentability dated Aug. 2, 2016 for PCT/IB2015/050646.
(Continued)

*Primary Examiner* — Adam Lee
(74) *Attorney, Agent, or Firm* — Andre Roland S.A.; Nikolaus Schibli

(57) ABSTRACT

The invention relates to a control device suitable for suggesting control instructions to the patient in order to facilitate the use thereof.

24 Claims, 7 Drawing Sheets

Figure 1:
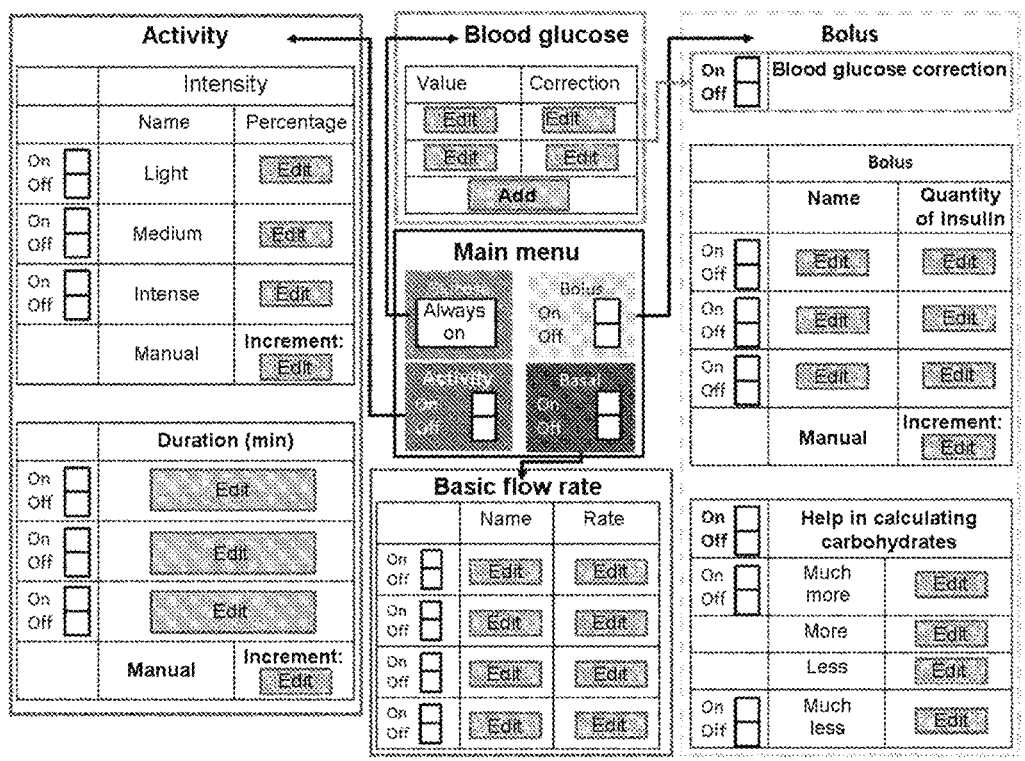

(51) Int. Cl.
*G16H 20/17* (2018.01)
*G16H 40/63* (2018.01)
*A61M 5/172* (2006.01)
*G05B 15/02* (2006.01)

(56) References Cited

U.S. PATENT DOCUMENTS

| | | |
|---|---|---|
| 6,656,114 B1 | 12/2003 | Poulsen et al. |
| 7,890,350 B1* | 2/2011 | Fiedotin .............. G06Q 50/24 705/3 |
| 7,941,200 B2 | 5/2011 | Weinert et al. |
| 9,171,343 B1* | 10/2015 | Fischell .............. A61M 5/1723 |
| 9,897,565 B1 | 2/2018 | Booth |
| 2002/0156464 A1* | 10/2002 | Blischak .............. A61M 5/14276 604/892.1 |
| 2003/0028089 A1* | 2/2003 | Galley .............. G06F 19/3456 600/365 |
| 2005/0022274 A1 | 1/2005 | Campbell et al. |
| 2005/0192557 A1 | 9/2005 | Brauker et al. |
| 2006/0047192 A1 | 3/2006 | Hellwig |
| 2006/0240166 A1* | 10/2006 | Al-Assaf .............. A61P 1/14 426/573 |
| 2006/0272652 A1 | 12/2006 | Stocker et al. |
| 2007/0072156 A1 | 3/2007 | Kaufman |
| 2007/0149861 A1 | 6/2007 | Crothall |
| 2007/0150025 A1 | 6/2007 | Dilorenzo |
| 2007/0213657 A1 | 9/2007 | Jennewine |
| 2008/0228056 A1* | 9/2008 | Blomquist .............. A61B 5/14532 600/365 |
| 2008/0269672 A1* | 10/2008 | Say .............. H01L 23/49548 604/66 |
| 2008/0300534 A1* | 12/2008 | Blomquist .............. G16H 10/20 604/66 |
| 2009/0006061 A1 | 1/2009 | Thukral |
| 2009/0105636 A1* | 4/2009 | Hayter .............. G16H 40/63 604/66 |
| 2009/0131861 A1* | 5/2009 | Braig .............. A61B 5/150862 604/66 |
| 2009/0157424 A1* | 6/2009 | Hans .............. G06Q 10/107 705/2 |
| 2009/0253973 A1* | 10/2009 | Bashan .............. A61M 5/1723 600/365 |
| 2009/0270833 A1* | 10/2009 | DeBelser .............. G06F 19/3468 604/500 |
| 2010/0121170 A1* | 5/2010 | Rule .............. A61B 5/14546 600/365 |
| 2010/0152713 A1* | 6/2010 | Adler .............. A61M 5/14276 604/891.1 |
| 2010/0185181 A1 | 7/2010 | Alme et al. |
| 2010/0262434 A1* | 10/2010 | Shaya .............. G16H 20/10 705/3 |
| 2011/0021898 A1* | 1/2011 | Wei .............. G16H 20/30 600/365 |
| 2011/0098548 A1* | 4/2011 | Budiman .............. G16H 50/50 600/365 |
| 2011/0112904 A1* | 5/2011 | Stupp .............. G06Q 30/02 705/14.58 |
| 2011/0124996 A1* | 5/2011 | Reinke .............. G16H 15/00 600/365 |
| 2011/0144586 A1* | 6/2011 | Michaud .............. F16J 15/56 604/151 |
| 2011/0224646 A1* | 9/2011 | Yodfat .............. G16H 50/70 604/504 |
| 2012/0027897 A1* | 2/2012 | Innocenzi .............. A23L 33/00 426/231 |
| 2012/0226259 A1* | 9/2012 | Yodfat .............. A61M 5/14244 604/500 |
| 2012/0232520 A1* | 9/2012 | Sloan .............. G01N 33/48792 604/504 |
| 2012/0245447 A1 | 9/2012 | Karan |
| 2012/0245556 A1* | 9/2012 | Kovatchev .............. A61M 5/1723 604/504 |
| 2012/0293328 A1* | 11/2012 | Blomquist .............. G16H 20/17 340/540 |
| 2013/0096530 A1 | 4/2013 | Budiman |
| 2013/0165901 A1* | 6/2013 | Ruchti .............. G06Q 50/22 604/504 |
| 2013/0283196 A1* | 10/2013 | Farnan .............. A61M 5/14244 715/771 |
| 2013/0331778 A1* | 12/2013 | Kruse .............. A61M 5/14244 604/66 |
| 2013/0332874 A1* | 12/2013 | Rosinko .............. G16H 40/63 715/771 |
| 2013/0338629 A1* | 12/2013 | Agrawal .............. G16H 50/70 604/504 |
| 2014/0276548 A1* | 9/2014 | Bollish .............. G06F 19/3468 604/503 |
| 2014/0328951 A1* | 11/2014 | Shim .............. A61K 31/704 424/728 |
| 2014/0347491 A1* | 11/2014 | Connor .............. A61B 5/681 348/158 |
| 2014/0349256 A1* | 11/2014 | Connor .............. A47G 21/02 434/127 |
| 2014/0349257 A1* | 11/2014 | Connor .............. G16H 20/60 434/127 |
| 2015/0126873 A1* | 5/2015 | Connor .............. A61B 5/4866 600/475 |
| 2015/0151050 A1* | 6/2015 | Estes .............. A61M 5/172 604/500 |
| 2015/0168365 A1* | 6/2015 | Connor .............. G01N 33/02 356/51 |
| 2015/0174209 A1* | 6/2015 | Chiquette .............. G16H 20/17 514/6.4 |
| 2015/0328403 A1* | 11/2015 | Dobbies .............. A61B 5/4064 600/364 |

FOREIGN PATENT DOCUMENTS

| | | |
|---|---|---|
| JP | 2009-521249 | 6/2007 |
| JP | 2007-525241 | 9/2007 |
| JP | 2005-215923 A | 8/2015 |
| WO | WO 2000/032258 | 6/2000 |
| WO | WO 2007/065285 | 6/2007 |
| WO | WO 2007/113708 | 10/2007 |
| WO | WO 2014/009876 | 1/2014 |

OTHER PUBLICATIONS

International Search Report and English translation thereof dated May 8, 2015 for PCT/IB2015/050646.
Japanese Patent Application 2016-548723 Notice of Reasons of Rejection dated Jul. 12, 2018.
Japanese Patent Application 2016-548723 Notice of Reasons of Rejection dated Nov. 7, 2017.
Written Opinion of the International Search Authority dated May 8, 2015 for PCT/IB2015/050646 (French).

* cited by examiner

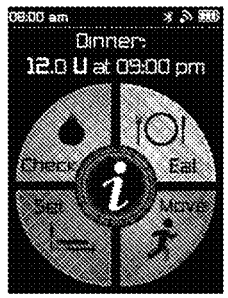 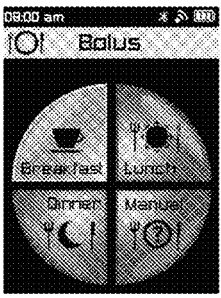 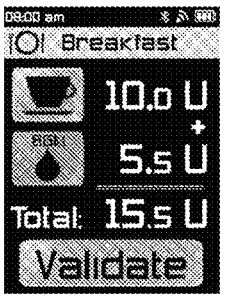 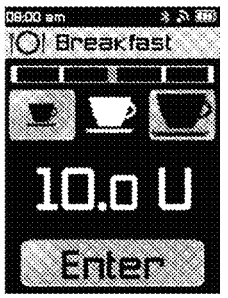
Fig. 3.1         Fig. 3.2         Fig. 3.3         Fig. 3.4
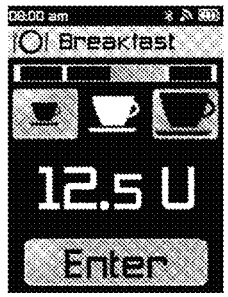 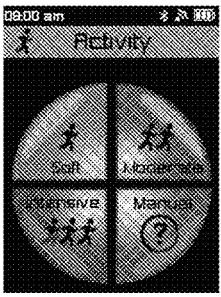 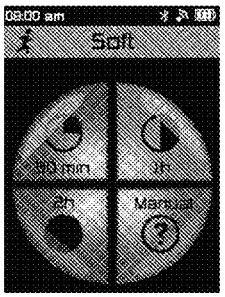 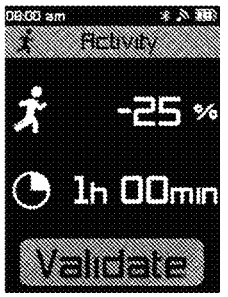
Fig. 3.5         Fig. 3.6         Fig. 3.7         Fig. 3.8
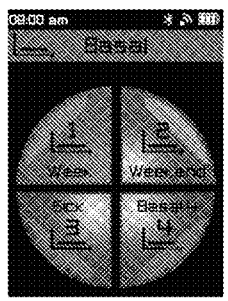 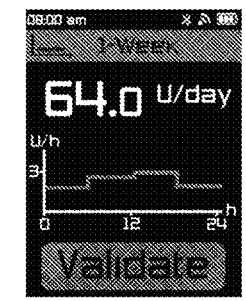
Fig. 3.9         Fig. 3.10

FIG. 8
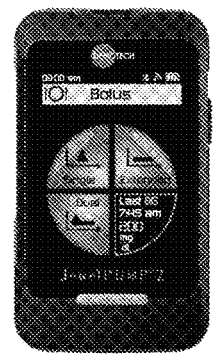   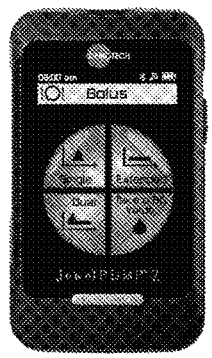   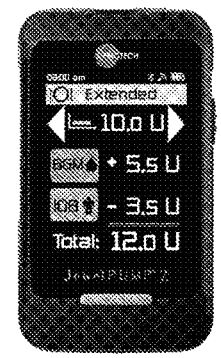
FIG. 9.1    FIG. 9.2    FIG. 9.3
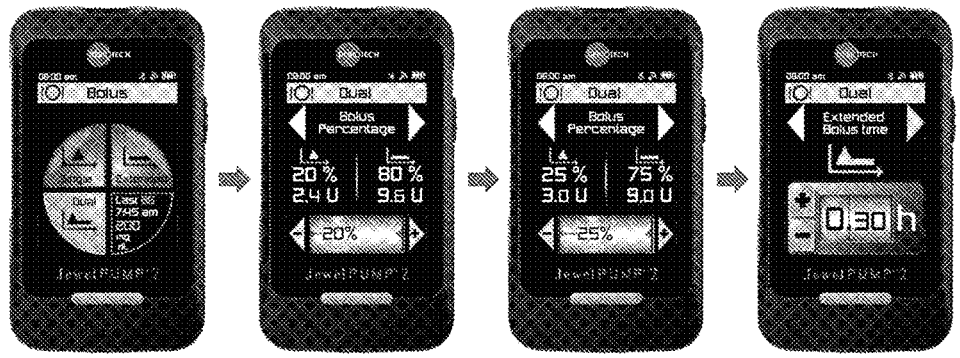
FIG. 10

CONTROL DEVICE WITH RECOMMENDATIONS

CROSS REFERENCE TO RELATED APPLICATIONS

The present application is a continuation patent application of U.S. application Ser. No. 15/114,423 filed on Jul. 27, 2016, that in turn is a United States national stage application of International patent application PCT/IB2015/050646 filed on Jan. 28, 2015 designating the United States, and claims foreign priority to European patent application EP14152955.2 filed on Jan. 28, 2014 and to French patent application FR1450706 filed on Jan. 29, 2014, the contents of all four documents being herewith incorporated by reference in their entirety.

FIELD OF THE INVENTION

The present invention discloses a medical treatment system and a method of using such a system comprising a control device suitable for controlling a medical device. It can be a control device comprising an interface making it possible to easily monitor and/or control a fluid delivery device.

STATE OF THE ART

Some treatments require the use of a delivery device which can be controlled by a control device (distinct or not from the delivery device), the two devices forming a medical treatment system. The delivery device can further make it possible to inject a medicine (pain relief, insulin, etc) or another fluid on or in the body of a patient. In the context, for example, of the treatment of a diabetic, a patient can use an insulin pump which will continuously and/or occasionally deliver a certain quantity of insulin.

The insulin-dependent diabetics, also called type 1 diabetics, no longer physiologically produce insulin. These people are therefore forced to track, with careful attention, their blood glucose and accurately and meticulously parameterize their insulin delivery device. This type of diabetes thus requires a device that provides them with a very comprehensive range of treatment options in order to monitor their sickness and live the best possible life.

There is another type of diabetes, called type 2 diabetes. The latter is characterized by an increase in resistance of the organism to insulin and a reactional hyper-insulinemia. The pancreas produces increasingly more insulin until it is exhausted and when the quantity of insulin is no longer sufficient to counter the resistances, the blood glucose becomes abnormally high. Type 2 diabetes can also require the use of an insulin delivery device. In this document, a delivery device should be understood to mean a delivery device comprising a tank and a pumping mechanism controlled by an electronic processor on the basis of instructions given by a control device. The PCT patent applications bearing the following numbers WO 2007/113708 A1 and WO 2014/009876 A2 respectively disclose a delivery device and a control device (comprising a communication securing mechanism), the full content of which should be considered to form part of the present application. However, the people afflicted with this type of diabetes are generally less disposed to use such a treatment system because it is too complicated to use. In effect, type 2 diabetics are generally more elderly, less at ease with the new technologies and are often from a socio-cultural background that is proportionally more under-privileged.

Generally, the existing treatment systems are very complex, requiring training and often hospitalization at the time of initialization of the treatment to carefully monitor the correct control of the system by the patient. This type of system is disclosed by the US patent applications US2006/272652 A1, US2005/192557 A1, US2010/185181 A1 or US2013/096530 A1 which are incorporated in this application for reference. These systems are restrictive and cannot be accessible to the whole world because of their complexity. For example, adapting a pre-prandial bolus according to the quantity of carbohydrates (to be estimated by the patient) which will be ingested, an option known by the name of "bolus calculator", remains an action that is very little used by some diabetics because of its complexity. Thus, these devices may not be suited to certain people despite the known advantages of these systems.

GENERAL DESCRIPTION OF THE INVENTION

The present invention is described and characterized by the independent claim or claims, whereas the dependent claims describe other features of the invention.

The present application claims the priority of the application bearing the following number EP14152955.2, filed on 28 Jan. 2014 in the name of Debiotech SA, the full content of which should be considered to form part of the present application.

The physiological and psychological characteristics are specific to each patient and are found to be highly heterogeneous between the members of a particular population (for example type 2 diabetics). Ideally, a treatment system should be suited to each patient in order to control a specific treatment taking into account all or some of his or her physiological and psychological characteristics. In order to offer such a system, the present invention discloses a control device comprising an interface that is easy to use, intuitive and it makes it possible to limit the manipulation errors. Ideally, the device offers such an interface without in any way neglecting the options and tools that allow for the best treatment of certain diseases or disabilities. The device can also, in one of its embodiments, incorporate a reminder functionality: in the case where the user might have forgotten certain steps of his or her treatment, the system can remind him or her thereof and provide a recommendation on the procedure to follow. Furthermore, the interface can be specifically edited for a patient taking into account his or her needs and his or her capabilities. Preferentially, the control device can enable the user to control a delivery device by using a specific incrementation rule.

The invention described in this document presents a control device suitable for controlling a treatment system which preferentially comprises a device for delivering a fluid to a patient. The control device can be distinct or not from the delivery device. In other words, the treatment system comprises a delivery device and a control device, these two devices can be arranged in one and the same casing or in two distinct casings and separate from one another. For example, the delivery device can be affixed to the body of the patient whereas the control device can be a remote control more or less remote from the delivery device. The control device can also be a personal computer. In all cases, the two devices (delivery device and control device) are suitable for exchanging information (data, instructions, etc) between them by wired or wireless means, for example via a radio communication, IR, etc). This communication can be one-way (from the control device to the delivery device) or two-way (at least between said devices).

The delivery device can be configured to deliver (but without being limited thereto) insulin, morphine, hydromorphone, bupivacain, clonidine, other analgesics, genetic agents, antibiotics, nutrient fluids, analgesics, hormones or hormonal medicines, gene therapy medicines, anticoagulants, cardio-vascular medicines or chemotherapy agents.

The control device is designed to control, check and/or monitor the delivery device. The control device comprises a display device and/or an input device (for example a touch screen) making it possible:

for the user to act on the system in order to control instructions (edit data, select or activate options and/or send commands for example: order the delivery of a fluid according to a flow rate, a quantity and/or a duration); and/or for the system to inform, alert, propose commands, prompt and/or recommend instructions to the user.

In this document, a user can be a patient, a doctor, a nurse, a person linked to the patient (a parent, a tutor, etc). Each type of user can have specific rights in the parameterizing and for the control of the system. For example, a doctor will be able to have access to certain parameterizings of the system whereas the patient does not have these same access rights. In this document, the prescriber is the user with the greatest number of access rights, the prescriber is preferentially a person different from the patient, for example a doctor, a nurse or a pharmacist.

It is particularly preferable to have this type of distinction when the patient does not have the capability or the competences or the knowledge needed for the correct control of the system. In the case where the person is not familiarized with the modern control devices, this type of system can make it possible for this person to have a simple and intuitive control offering only controls that he or she really needs.

According to a first aspect of the invention, a treatment system comprises at least two distinct interfaces. In this document, the term "interface" should be understood to mean: a device allowing for the exchange of information between a user and an electronic system (for example, the control device or, more generally, the treatment system). This device can comprise an input device and a display device. The input device can enable a user to send (inform, notify) information to the processing system and the display device can enable the system to send (inform, notify) information to the user. In the case where the system comprises a touch screen, the input and display devices are at least partially combined in the touch screen. The first interface is accessible only to a prescriber and the second interface is accessible to another type of user (for example the patient or the tutor of a patient). The access to at least one interface can be secured and locked by a password or specific token (bar code, fingerprint, RFID chip, pin code, etc). The first interface allows access to a greater number of parameterizings. Thus, for example, a doctor can edit certain values or activate options that the patient will not be able to modify because of his or her limited access rights.

Furthermore, it is particularly advantageous to limit certain functionalities of the control device in the case where the fluid administered might be dangerous to the patient. Thus, the patient will be limited in his or her controls in order to avoid him or her administering or controlling, knowingly or unknowingly, a lethal dose (for example, if the fluid is insulin).

In one embodiment, these two interfaces can be present on the same control device and/or on two distinct control devices. In this case, the prescriber interface will be able to be available on the control device of the prescriber (for example, a personal computer or another specific or nonspecific device) and the patient interface will be able to be available on the control device of the patient. Furthermore, the parameterizing data (modified by the prescriber) will be saved by the treatment system so that these data can be used by the control device of the patient.

Preferentially, the control device of the patient can display the two interfaces so that the prescriber can modify data via the control device of the patient.

It may be possible to envisage having three distinct interfaces, for example when the patient has reduced capabilities. The first interface would be accessible to the doctor, the second interface might be accessible to a responsible person (a parent, a tutor, a pharmacist, a nurse, other responsible personnel) and a third interface would be accessible by the patient. A responsible person is a person having the capacity, the knowledge and/or the competences necessary to receive specific access rights. These access rights are lower than the access rights of the prescriber but higher than the access rights of a patient who would not be capable or sufficiently competent. This intermediate interface is additional and optional, it depends primarily on the patient treated. The prescriber could have access to all three interfaces, the responsible person could have access to two interfaces (his or her own and that of the patient) while the patient would have access only to a single limited interface. This kind of hierarchy is found for example when the patient is a child or a handicapped person.

Generally, some interfaces could be accessible via an access code known only to or in the possession of the prescriber (a doctor) or a responsible person. Using the prescriber interface, for example following an assessment, the prescriber can edit various parameters of the treatment in order to match the needs and capacities of the patient. Thus, the prescriber can pre-enter data (such as, for example, a basal profile or a predetermined quantity for a bolus) and the patient interface makes it possible to select these pre-entered data (to select a basal profile or to control a bolus infusion for example). Preferentially, the patient interface allows the patient to marginally adjust the pre-entered data (for example to increase or reduce the bolus quantity to be infused).

In one embodiment, the prescriber interface makes it also possible to parameterize a user interface. Thus, the prescriber can personalize a user interface (for example the patient interface) guaranteeing an appropriate use and treatment. In other words, the prescriber could activate certain options allowing another user to have access to certain functionalities, such as the adjustment of the treatment.

According to a second aspect of the invention, the control device is suitable for proposing an interface that is intuitive and easy to use allowing a user to easily control the delivery device and optionally be able to marginally adjust the treatment.

Some treatments need to be adapted according to the lifestyle of the patient, in other words according to his or her activity. "Activity of the patient" should be understood to mean the action carried out by the patient during a period. This period can be the present, a recent past or new future to the present or at least a period during which the effect of the activity on the patient (for example his or her blood glucose) must be taken into account. It can be a temporary physical activity, the taking of a meal, a temporary rest, an activity during a day or several days. For example, in the case of diabetes, a patient does not have the same needs for insulin throughout the day, or according to his or her activity or his or her state of health. In effect, the blood glucose of a patient fluctuates, for example, the blood glucose will be dependent on the type of meal and the quantity of food ingested. When the patient is sick or if he or she is currently performing a physical effort, his or her insulin needs to regulate his or her blood glucose will be substantially different. Thus, for patients who are less regular or who have a poor knowledge of their needs, it is often very difficult for them to follow their treatment. All the more so when, in the case of treatment for diabetes, the patient may need basal and bolus injections that are difficult to calculate.

Throughout the description of the present document, the term basal is commonly used to describe the basic flow rate infused to a patient over a long duration, for example a day. The basic flow rate can be variable over time because the insulin needs differ throughout the day and depend also on the sensitivity of the patient to the insulin which also varies over time. The basal is often contrasted with the bolus which is a delivery of a determined quantity over a relatively short duration compared to the basal, for example a few seconds or minutes.

Thus, the control device includes a graphical interface suited to the patient, this control device comprises a set of commands illustrated on a first screen. This set of commands is preset so that the patient now only has to activate or select a command for it to be executed without being constrained to enter an entire series of data in order to control the delivery device. For example, the devices of the prior art require the patient to complete several fields (e.g. carbohydrates ingested during the meal, type of food (red meat, bread, salmon, etc), the quantity in grams ingested, delivery flow rate, time of delivery, sensitivity to the medicine as a function of the time of delivery, etc) in order to control the delivery of the fluid. Now, according to the second aspect of the invention, the control device avoids these constraints and greatly simplifies the life of the patient.

Optionally, this set of commands can be adjusted by the patient marginally. This adjustment can be done by predetermined increment. Preferentially, the prescriber will have previously parameterized the control device so that the treatment is matched to the patient and the possible adjustments will be limited according to rules established by a doctor and/or a qualified person (carer, responsible person, etc).

This aspect of the invention makes it possible in particular to:

limit the number of errors in the commands performed by the patient;
simplify the use of the control system;
speed up the takeover by the patient.

Optionally, the system saves the history of the actions (measurement, bolus control and/or quantity delivered) so as to limit or prohibit an additional command which could be damaging to the health of the patient.

In one embodiment, the patient can request the execution of a bolus delivery command before or after or during a meal. The patient actuates this command by simply pressing on the type of meal (breakfast, lunch, dinner, supper, snack, etc) that he or she has ingested. Previously, the doctor (prescriber) will have entered a set of typical boluses which depends on the type of meal or time of the meal or on the bolus command and not dependent on the type of food ingested. The difference lies in the fact that the patient has a limited choice (breakfast, lunch, dinner) unlike the other known systems which request information which is often not understood by the patient (quantity of carbohydrate) or that is difficult to estimate or recognize (weight of the food, type of food, etc). This is thus a major advance for the patient which, through its simplicity, prompts him or her to use his or her control device. Depending on the needs and the capacities of the user, it may be advantageous to also propose a bolus command simply by entering the quantity to be injected.

It may also be useful for the system to automatically recognize (based on the time and/or the meal previously counted), whether it is a breakfast, a lunch or a dinner, thus simplifying the control steps while reducing the risk of errors. Thus, the type of meal could be suggested by the system, the patient optionally being able to accept the type of meal proposed or change it.

In other words, according to one embodiment, the control device is suitable for proposing a bolus command as a function of the type of meal that the patient should or would have ingested. For example, when the patient commands a bolus when he should be ingesting a breakfast (i.e. at the usual times at which a breakfast is traditionally taken), the control device will propose a quantity of insulin which will be adapted to meet the needs linked to a breakfast. This type of meal can be informed by the user (as prescribed above) or determined or proposed by the control device according to the time of day (for example according to a time band or preceding meal). Thus, the control device could be suitable for proposing a delivery command according to the time of the day when the patient commands this delivery.

Optionally, the control device stores the meals or the meal types ingested using a memory connected to the processor of the control device. Thus, upon the next bolus command, the delivery device will be able to compose a bolus suited to the next meal. For example, if the patient ate at 6:00 am then at 11:30 am, the control device will be able to propose a first bolus suited to a breakfast and a second bolus suited to a lunch. Thus, the device is suitable for proposing a certain quantity of insulin according to a time band and/or according to the meal previously ingested.

The system can also make it possible to remind the patient that a bolus must be administered if a delay is exceeded since the last bolus. According to one embodiment, the control device can prompt a patient to order a bolus when a time band corresponding to a meal has passed without the patient having ordered bolus delivery.

According to one embodiment, in order to propose an easy adjustment of a bolus command, the present invention can replace the calculation of the carbohydrates by a simplified concept of increment according to the size of the portion of food eaten relative to a reference plateau. The patient can simply adapt his or her bolus by indicating whether he or she is eating "a little more", "much more", "a little less" or "much less", modifying the initial bolus according to increments that have been pre-edited, for example by a doctor (prescriber). The increment can take account of the sensitivity of the patient to insulin according to the time of day (for example: time of day, a day can comprise up to 24 hours).

According to one embodiment, the basal can be modified (temporarily or not) by the user simply by selecting a profile or by entering his or her state (sick, etc). Preferentially, the prescriber will first have entered a set of data that the user will be able to use simply by actuating this control. Also, a control device can comprise a prescriber interface, for example as described in the first aspect of the invention. The prescriber interface makes it possible to define/edit one or more basal profiles while the patient interface makes it possible to select the appropriate basal profile.

In the present document, a basal profile is a succession of flow rates which will be executed over time (a day for example) by the delivery device. This succession of flow rates can be a succession of constant or variable flow rates. Each flow rate depends on the need of the patient at a time T and defined by a prescriber. In other words, the prescriber defines (preprograms) different basal profiles that the patient selects and actuates according to the type of day (working day, weekend, etc) and/or his or her physiological state (sick, etc). The patient interface thus comprises a set of commands preprogrammed by a prescriber and that can be actuated by the patient. Thus, the patient is not forced to estimate his or her treatment needs for the day but he or she simply has to inform the system as to the type of day (holiday, working, sick, etc) to come or in progress.

According to one embodiment, the patient will be able to have access to options for temporarily adjusting his or her treatment, for example to take account of an activity performed temporarily by the patient. It can be a sporting activity or at least an activity which would cause his or her blood glucose to decrease (substantially or not). Also, if the system did not take account of this lowering of blood glucose caused by the activity of the patient, the patient would risk entering into hyperglycemia. This is why a patient must reduce or stop the delivery of insulin during such an activity. Now, an unaccustomed patient cannot estimate the reduction of his or her insulin needs because, to do this, he or she would have to perform complex calculations. Thus, the system makes it possible to reduce the delivery of insulin not according to an undesirable quantity of insulin but according to a concept that is more familiar and intuitive for the patient, such as the intensity of the activity and/or the duration of the activity.

This differentiation is vital because, for an unaccustomed patient, reducing the delivery of insulin by 20% or by 50% is not representative. However, it is easier and more intuitive to inform of the intensity of the physical activity and/or its duration. In other words, the patient is no longer forced to estimate his or her reduced insulin need but he or she must simply inform the control device of his or her effort (for example the intensity and/or the duration of the activity). Preferentially, the reduction of delivery of insulin will be proportional to the effort and parameterizable via a prescriber.

In other words, by virtue of the informing of an event undergone and/or performed by the patient, the treatment system will perform an action beneficial to the treatment of the patient.

According to a third aspect of the invention, the control system comprises an interface that is simplified and organized so that the patient quickly and intuitively recognizes the commands.

In one embodiment, the graphical interface comprises a succession of screens, at least two of which substantially identically illustrating a set of commands. In other words, at least two screens comprise at least two distinct commands, said distinct commands of the first screen having similar graphical characteristics (color and/or form) to the commands of the second screen. For example, a first screen and a second screen present four commands that can be actuated by the user and each representing a part of a disk (for example a quarter disk).

The graphic illustrations of the commands presented above can have distinctive signs making it possible for the patient to easily, rapidly and unequivocally identify the type of command, such as, for example, a color code, a logo, a pictogram, a text, a form and/or a zone dedicated to the type of command, etc.

According to a fourth aspect of the invention, the command can have communication means making it possible to transmit certain data (action of the patient, actual delivery, blood glucose measurement) and to check, remotely, the compliance (observance or correspondence) of the patient to the treatment. It can, for example, concern means for checking, by a doctor or a nurse, elements of the treatment and/or messages received in case of poor compliance of the patient to the treatment (for example bolus or blood glucose measurement not performed or forgotten). This is in order to be able to remind the patient and indicate to him or her the procedures to be followed before the effects of the poor compliance have repercussions on the state of health of the patient.

In this document, the term compliance is defined as the behavior which consists in correctly following the prescriptions for use of the medicines.

The different embodiments presented in this document can be combined in order to obtain all or some of the advantages of these embodiments.

LIST OF THE FIGURES

To allow for a better understanding of the invention, one or more embodiments will be described, illustrated by the figures attached to this document. It goes without saying that the invention is not limited to these embodiments.

Figure 2:
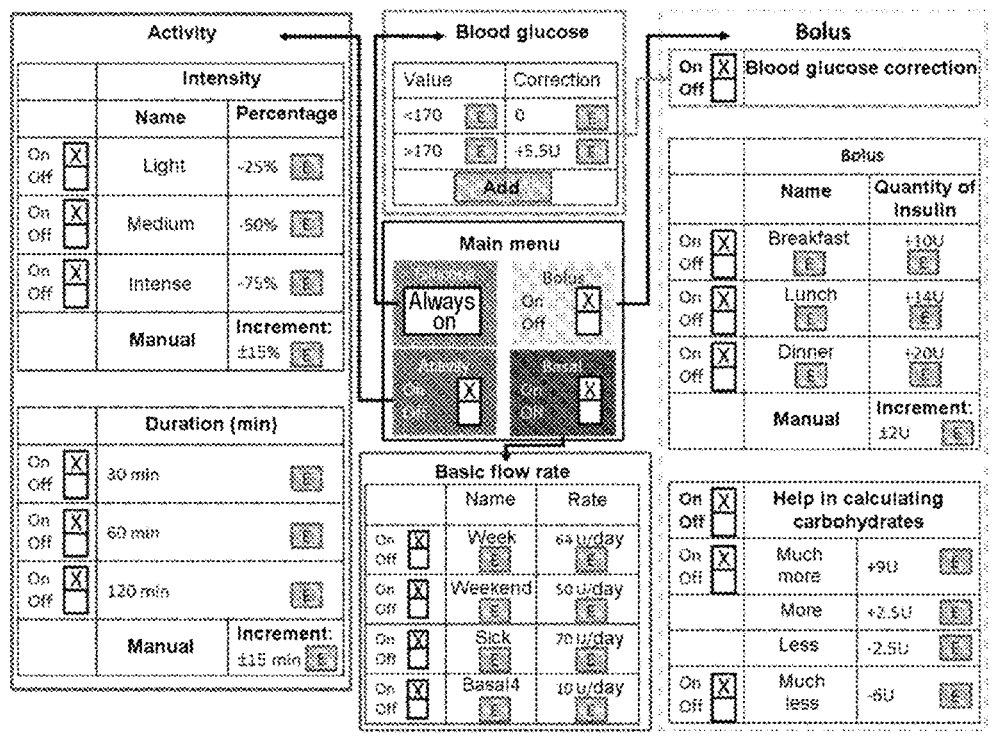
Figure 4:
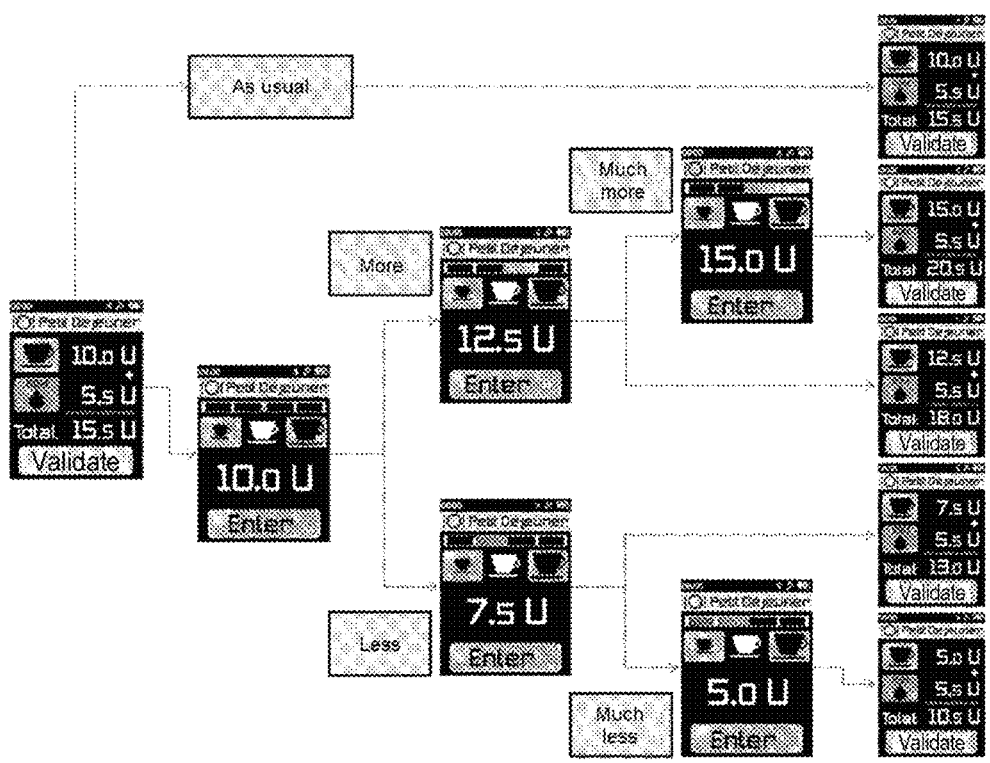

FIG. 1 schematically represents the user parameters that the prescriber can edit;

FIG. 2 illustrates an example of parameterizing;

FIG. 3 discloses possible display screens for the user;

FIG. 4 explains the different command instruction modification paths via the user interface.

Figure 5:
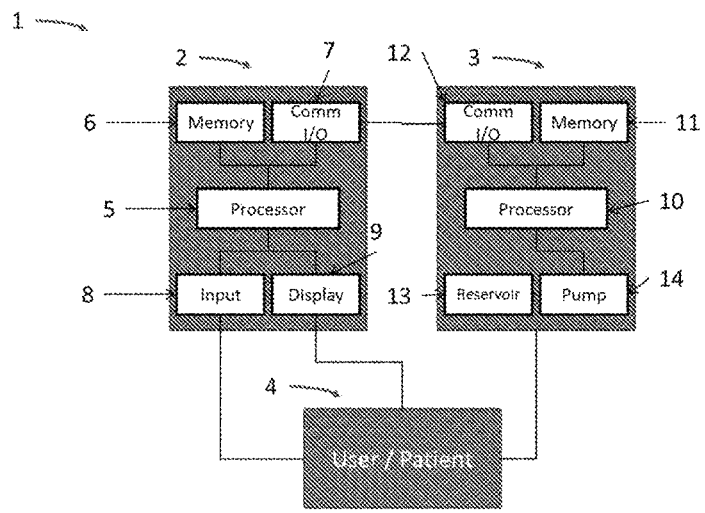

FIG. 5 schematically illustrates a treatment system comprising a control device and a medical device.

FIGS. 6 to 13 explain examples of a screen displayed by a control device.

LIST OF ELEMENTS

1 Treatment system
2 Control device
3 Delivery device
4 User/patient
5 Processor
6 Memory
7 Communication means
8 Input device
9 Screen
10 Processor (if necessary)
11 Memory (if necessary)
12 Communication means
13 Tank (optional)
14 Pumping mechanism (optional)

DETAILED DESCRIPTION OF THE INVENTION

In the present document, the detailed description of the invention comprises embodiments of devices, of systems and of methods given by way of illustration. It is clearly understood that other embodiments can be envisaged and can be provided without departing from the scope or the spirit of the invention. Consequently, the following detailed description should not be taken in a limited sense.

Unless otherwise indicated, the scientific and technical terms used in the present document have meanings commonly used by those skilled in the art. The definitions provided in this document are mentioned in order to simplify the understanding of the terms frequently used and are not intended to limit the scope of the invention.

The verbs "have", "comprise", "include" or equivalent are used in the present document in a broad sense generally signifying "includes, but without being limited thereto".

GENERAL DESCRIPTION OF A POSSIBLE EMBODIMENT

FIG. 5 discloses a medical treatment system (1) suitable for administering a treatment to a patient (4). The treatment system comprises a control device (2) and a medical device which is preferentially a delivery device (3). FIG. 5 schematically represents the system with a control device (2) distinct from the delivery device (3). However, these two devices can be arranged in the same casing, not represented here. In the case where the two devices are not distinct, the system could comprise a single processor and/or a single memory. In this document, the memory can be of RAM, ROM, NVRAM, EEPROM or flash type or any other type of memory known to those skilled in the art.

The control device (2) comprises a processor (5) that can be connected to a memory (6), communication means (7), an input device (8) and a screen (9). The control device can be a personal computer, a cell phone, a diabetes management system, a BGM, etc. It can be of a form that is small enough to be held in the hand of the user and/or in his or her pocket. The memory (6) can further make it possible to save control instructions preprogrammed by the prescriber, the control instructions previously executed and/or the different actions, activities and information informed by a user.

The delivery device can comprise a processor (10) that can be connected to a memory (11), communication means (12), optionally a tank (13) and a pumping mechanism (14). Also, the delivery device can be adapted to inject into a patient (4) a fluid contained in the tank (13) using a pumping mechanism (14).

A user (4) can be a prescriber, a patient or another person. The patient is the person who receives the medical treatment and interacts with the system whereas the other users are people who only interact with the system.

The system can comprise several control devices. For example, the system can comprise a control device reserved for the sole use of the prescriber and a specific control device for the patient. Ideally, the control device of the patient is more easily transportable and is of a size small enough to be contained in a pocket. Its height can be between 160 mm and 50 mm, its width between 90 mm and 30 mm and its depth between 5 mm and 30 mm, ideally it measures approximately 95 mm×60 mm×15 mm to +/−5 mm. Preferentially, said control device of the patient comprises at least two different graphical user interfaces, one that can be accessed only by the prescriber and the other accessible to the patient.

The patient interface can be the basic interface whereas the prescriber interface is accessible only with a specific identification means. A basic interface should be understood to be the interface which is accessible directly or initially as soon as the control device is started up, switched on or awoken from standby. However, it is possible, upon first startup of the control device (that is to say before the prescriber has parameterized the control device in order to adapt it to the patient), for the first interface to be that of the prescriber. However, after the parameterizing, the user interface will be able to become the basic interface.

The control device (2) and the delivery device (3) comprise communication means (7, 12) enabling them to exchange data by wired or wireless (radio wave, Bluetooth®, IR, wifi, etc) means. These data can be, for example, an instruction sent by the control device to the delivery device in order for the latter to execute a determined action (selection of a basal profile, injection of a bolus, reduction of the basal profile, modification of the basal profile, etc). The communication means (7, 12) can be adapted to transmit or exchange data with another remote device, such as the computer of a prescriber or a medical server, etc. The communication can be performed by any means known to those skilled in the art, such as via an RJ45 port, USB, by wifi or GSM (3G or 4G). If there are several control devices, the latter can also communicate with one another. For example, if the prescriber parameterizes or programs the system with a specific control device (for example, a personal computer) then the control device of the prescriber will be able to send the parameterizing data to the system, for example directly to the control device of the patient.

The user (4) uses an interface to control the treatment system (1), this interface comprises a screen (9) and an input device (8). The interface is adapted to the user so as to offer options and functionalities that are only necessary to, and understandable by, the user. The input device (8) can be a button, a voice command, a glucose measurement means (BGM or a CGM), a keyboard, a mouse. The screen (9) and the input device (8) can form a touch screen.

Examples of an Intuitive Treatment System According to the Invention

One of the main benefits of the invention is that a prescriber has the possibility of assigning a pre-established specific action to a key (input device (8)) in order for a user (for example the patient, whether young or elderly) to be able to press on this key without worrying about the program of the action which will be performed by the system.

In the context of the treatment for diabetes, the invention is particularly suited to at least three types of instructions that a patient may be required to use regularly:
  ordering a bolus during a meal, and/or
  designating a basal profile, and/or
  adjusting the basal profile according to the activity of the patient.
Ordering a Bolus:

In order for the ordering of a bolus on the occasion of a meal to be usable by most diabetics (including type 2 diabetics), it is important for the use of this tool to be simplified and require only very little thought on the part of the user.

Thus, the control device can comprise an input device that allows the patient to enter not the quantity of insulin to be injected but the type of meal which he or she has ingested or will ingest. The control device thus presents at least one type of meal of the day (breakfast, lunch, dinner, etc). The patient (or other user) selects the corresponding type of meal in order to obtain the appropriate treatment. Previously, the prescriber will have saved at least one standard treatment corresponding to a standard meal.

As presented in FIG. 3.2, the control device displays a patient interface showing the different types of meal that the patient can select. Optionally, the control device can offer/ suggest a type of meal according to the meal previously informed and/or according to the time of the day (in this case, the control device can comprise an internal clock).

This bolus preprogrammed by the prescriber can be adjusted according to several options:
by taking into account the blood glucose of the patient, and/or
by adjustment according to the quantity ingested.

Taking into Account the Blood Glucose of the Patient

If the patient has measured his or her blood glucose, the system will be able to offer a correction making it possible to adjust the bolus according to the blood glucose (of the patient) measured previously. FIG. 3.3 shows the patient interface with a correction of the bolus linked to the measured blood glucose of the patient. It concerns in particular the information displayed to the right of the icon illustrating a droplet also including the annotation BGM. The patient will optionally be able to accept or not accept this correction, for example by pressing on the corresponding key or icon (in this document, the terms icon, logo or pictogram are used interchangeably). This correction can take effect if the blood glucose measurement has been performed within a certain time period preceding the present bolus command. If this time period is exceeded, then the control device will be able to prompt the patient to perform a new blood glucose measurement, for example by pressing on the corresponding key, pictogram or icon. Furthermore, the input device (8) of the control device can be used to inform of the blood glucose of the patient. It can be a simple keyboard (on which the patient enters the measurement performed with another device) or a blood glucose measurement means (BGM, CGM) not represented in the figures.

Adjustment According to the Quantity Ingested

Still with the aim of simplifying the use of the treatment system (1) by the patient, the invention proposes that the patient only has to estimate if he or she is eating as usual, more or less than usual or much more/much less than usual. This estimation of the quantity ingested of the type of meal makes it possible for the system to adjust the quantity of insulin to be injected.

Once again, the input device (8) makes it possible to inform the control device of the quantity ingested. The control device can graphically illustrate this option using + or − signs but also by using icons representing a certain meal quantity as disclosed in FIG. 4. FIG. 3.4 illustrates the graphical interface of the patient. The icons in cup form represent the type of meal (here a breakfast), and it will also be noted that it is a graphic representation substantially identical to that of FIG. 3.2 that the patient has selected (highlighting of the selected icon).

FIG. 3.2 represents the patient graphical interface. The breakfast icon is highlighted and the others are grayed out. This highlighting of an icon can reflect the fact that the patient has selected this icon or can be a proposal from the control device. In the latter case, the patient will simply have to validate this proposal or select another type of meal.

According to one embodiment, the patient now only has to touch the smallest or largest cup to inform of the quantity ingested in the breakfast. For information, the graphical interface also presents the adjusted quantity of insulin. Thus, the patient can check that this value is indeed consistent. That makes it possible to reassure the patient, inform as to the quantity calculated but also make the patient aware of the quantity of insulin necessary. Thus, the patient learns his or her insulin needs through practice, making it possible for him or her, in case of failure of his or her system, to approximately assess his or her insulin needs.

Preferentially, the patient can enter this information according to the incrementation prescriptions previously programmed by the prescriber. In other words, the prescriber will be able to previously parameterize the increments increasing or reducing the quantity of insulin. These increments are used when the patient adjusts the quantity of meal ingested.

This approach requires little involvement on the part of the patient who can correct his or her bolus according to the size of his or her meal in 3-4 presses with no carbohydrate calculation requirement. This image-based approach makes this tool accessible to all (children, elderly people, patients with cognitive deficiencies, etc).

FIG. 4 shows a flow diagram which illustrates a succession of screens of the patient interface when he or she informs the control device of the quantity of meal ingested.

In reality, through the patient interface, the latter does not order an injection but informs the system of an event (of an action performed or which will be performed by the patient) which is, here, the taking of a meal. The aim of the system is thus to adapt the therapy according to information given by the patient. In other words, the processor uses a mathematical model adapted by the prescriber (incrementation, degree of sensitivity to insulin, etc) which takes into account the type of meal ingested by the patient. The mathematical model can also take into account the quantity ingested and/or a measurement of blood glucose of the patient.

Designation of a Basal Profile

In the prior art devices, the patient creates, with the help of a doctor, a profile of flow rates which will be infused throughout the day. This is the basal profile. Normally, the patient has the possibility of modifying the basal profile but this is very complicated and can lead to a substantial modification of the treatment. Also, this action can be relatively dangerous for the patient. An unaccustomed person will not have sufficient competences to modify this basal profile for all the treatment has to be able to be adapted according to the day because the insulin needs can vary according to different parameters. Some devices make it possible to save several basal profiles but it is not obvious to an uninitiated person how to recognize the profile which is suited to a given day.

To eliminate this drawback, the invention proposes to easily and comprehensively presenting at least two basal profiles. Thus, the control device makes it possible to identify each profile according to a typical day or a physiological state of the patient. Each typical day represents the usual activity of the patient during that typical day (for example: working type day, typical day when the patient is on holiday or sick, etc). In other words, as illustrated by FIG. 3.9, the patient interface presents the basal profiles according to at least two typical days (for example, on this screen, it is possible to distinguish two typical days: a working week or weekend) and/or according to the state of health of the patient (for example, on this screen, it is possible to select the typical day: sick). The screen 3.10 makes it possible to inform the patient of the exact profile (that is to say the basal rate profile) before the latter validates this option.

In the case where the system comprises an internal clock, the device can suggest a basal profile. For example in FIG. 3.9, the first icon is highlighted and the others are grayed out; that can be due to the fact that the patient has selected this icon but that can also be a suggestion on the part of the control device. Thus, depending on the day of the week for example, the device may suggest a typical day that the patient will be able to validate or not as for the type of meal described above.

Thus, the patient does not select a basal profile but informs the control device as to the current type of day and/or his or her state of health. Previously, a prescriber will have parameterized or programmed at least one typical day corresponding to a basal profile adapted to the patient according to this typical day.

Temporary Adjustment of the Basal Profile According to the Temporary Activity of the Patient:

A basal adjustment option can be used over a relatively short period. This involves adjustment according to the temporary physical activity of the patient.

Thus, the control device presents, via its patient interface, an adjustment option allowing the patient to inform of his or her temporary physical activity via the input device. The temporary physical activity is an activity performed (or which will be performed) by the patient for a limited duration (for example: a few minutes to a few hours but strictly less than 24 hours). It can be sport, a stroll or any other unusual physical activity on the part of the patient which would cause his or her blood glucose to lower. The input device can further make it possible to inform of the amplitude of the effort such as, for example, the intensity and/or the duration of this activity. The simple fact of actuating this option will lead to a modification of the infusion (in this particular case, a reduction of the insulin infusion).

In order to allow this functionality, the control device comprises an input device allowing a user (for example a patient) to inform of the temporary effort of the patient so that the system temporarily adapts the treatment according to these data. The control device thus presents an "activity" option which, upon the activation thereof, allows the patient interface to display at least one screen prompting the patient to assess intensity of the physical activity and/or the duration of this activity. An illustration of these screens is presented by FIGS. 3.6 and 3.7. FIG. 3.8 presents a summary prior to validation of the adjustment; it makes it possible to inform the patient of the instruction which will be sent to the delivery device.

Preferentially, the control device proposes at least two intensity levels. The prescriber will have previously predetermined the impact of this activity according to the intensity level and/or the duration. The processor can also comprise a mathematical model making it possible to achieve the same end. In other words, the system can make it possible to calculate an adjustment of the treatment according to the intensity and/or the duration of the physical activity.

To sum up, the patient is no longer concerned with the programming, but informs the control device of his or her activity (eating, sick, type of day, physical activity) provoking a reaction preprogrammed by the prescriber.

Examples of Use of the Prescriber Interface

Initialization

In one embodiment, upon first use of the interface, an administrator (or prescriber) code, previously given to the treating doctor (or prescriber), is requested in order to establish the first user parameters which are listed in FIG. 1.

Example of Parameterizing

Each of these parameters can be personalized by the treating doctor (prescriber) according to the needs of the patient (for example in FIG. 2) and the parameterizing of these options will define the final interface obtained (for example in FIG. 3). While the patient can request the execution of the control instructions, it is impossible for him or her to paramterize said control instructions, that is the exclusive role of the prescriber. In the following example, the specific parameterizing chosen will define the interface that the user will be able to manipulate without being able to edit it.

Figure 7:

To access the parameterizing, the user must specify what type of user he or she is, for example like the left-hand image of FIG. 7. In this image, the system can comprise at least two different types of users (patient, caregiver, health care professional) and thus with different access rights. Preferentially, the patient will not be able to access any parameterizing option. In one embodiment, if the patient has sufficient knowledge, the prescriber will be able to choose to give him or her access to certain parameterizing. After the selection of the type of user, the latter must enter his or her personal code (for example a PIN code) then a parameterizing screen will be displayed (right-hand image of FIG. 7). FIG. 7 thus describes the succession of screens to access the parameterizing of the system.

Modification of Parameters and Influence on the User Interface

The possibility of being able to activate or else deactivate most of the options will therefore have a great impact on the user interface. Take the example of a patient who, according to the treating doctor, does not use the "activity" option, he or she can deactivate it (set this option to off) and thus influence the design of the user interface. Similarly, if a treating doctor estimates that this tool (pump and remote control) is suitable to treat a diabetic child only via the use of the "set" (basal) option, he or she can make the other options (bolus and activity) inactive thus modifying the user interface. This aspect of "activation if there is a need" will make it possible to remove the unused options which could disturb the patient. This offers a great advantage because the doctor can then prescribe a pump treatment to a person who has a cognitive deficiency without in any way running the risk of the latter using options which could be hazardous or even fatal to him or her.

Furthermore, the prescriber interface makes it possible to act on:
- the activation of the bolus, basal and/or activity options (see the middle of FIG. 1). In the case where these three actions would be inactive then the control device would allow the patient only to measure his or her blood glucose using an input device (e.g.: a specific sensor) and/or to have access to the actions history; and/or
- the activation of the activity intensity levels (at least two, for example: light, medium, intense) and/or duration options (for example: 30 min, 1 hour, etc), an example of a graphical interface is disclosed in FIG. 8; and/or
- the increments of the intensity and/or of the duration; and/or
- at least two (ideally four: for example: weekend, week, holidays, sick) basal profiles of which the headings and the data can be parameterized by the prescriber; and/or
- at least two (ideally three and optionally the possibility of doing a manual input) types of meal: their heading and the respective quantities of insulin; and/or
- the increments of the bolus option (whether for the manual option or for the adjustment of the quantity)
- the activation of the taking into account of a blood glucose measurement and/or the duration of validity of this measurement; and/or
- the blood glucose measurement options.

Ultimately, the invention offers the user an interface which can be modulated by an administrator (who is the prescriber for example) according to his or her needs and his or her capacities. This therefore opens use of the insulin pump to a very wide population.

Example of Overall Parameterizing

FIG. 2 illustrates the final parameterizing performed by a prescriber. Also, the control device will enable the patient for example to reduce by 25% the quantity of insulin for 30 minutes during an activity, or to order a dose of 14 units during a lunch and to uprate it by 2.5 units if the lunch is relatively large.

Example of Parameterizing by the Treating Doctor for the Bolus Options

Using this simplified bolus command, the system is programmed in advance by a prescriber via a specific interface allowing the prescriber to save the necessary treatment adapted to the patient according to the type of meal that he or she will come to ingest in a day.

The incrementation parameters according to the estimated quantity of food are previously edited by the treating doctor (prescriber). For example:

| | Meal | | | |
|---|---|---|---|---|
| | "I eat much less" | "I eat less" | "I eat more" | "I eat much more" |
| Bolus correction | −5.0 [U] | −2.5 [U] | +2.5 [U] | +5.0 [U] |

Examples of Patient Interfaces

FIGS. 3.1 to 3.10 show a set of screens that can follow one another and which are used by the patient graphical interface.

FIG. 3.1 shows a screen which can be the basic screen, that is to say the main screen which is displayed when the control device is switched on or woken up from standby. A first top strip can provide information to the user as to the time and the status of the elements of the device (for example the reception level, the battery level, etc). A second specific zone makes it possible for the user to know the last meal informed and, optionally, the quantity of insulin injected by the delivery device. If no correction or adjustment has been made by the user then it is also the quantity of insulin associated with this type of meal. Most of the screen is devoted to the main command options. These commands allow the user to inform the system regarding:

the blood glucose measurement. Using this command, the patient will be able to inform the control device of his or her blood glucose level at a given moment. This information is informed using an input device which can be a set of keys, a keyboard, a specific sensor (those used for example by the BGMs or the CGMs known to those skilled in the art). In the latter case, when the patient has selected this command, the graphical interface will display a succession of screens comprising fixed and/or animated images with a text explaining the procedure to be followed. The patient will also be able to specify whether the blood glucose measurement was performed before or after a meal. All of this information will then be saved in the memory of the control device so that the user can review a measurement and/or the doctor can also track the curve of the blood glucose of his or her patient. This information can also be sent to a dedicated medical server for the patient to be tracked as accurately as possible; and/or the taking of a meal; and/or the temporary physical activity of the patient; and/or the current type of day.

According to one embodiment, these four commands are arranged in four disk quarters (or arcs of a circle). Each command is represented by a quarter disk in which there can be a graphical illustration, information and/or text. Each command can have a specific color. For example, the blood glucose measurement can have an icon (quarter disk) with a green background color, the meal in yellow, the activity in blue and the type of day in violet.

Access to the History Option

At the center of this command disk (or arc of a circle) of the basic screen there is, according to FIG. 3.1, a circle with a character representing an "i". This circle (or icon, or pictogram) makes it possible to access a command displaying the history. As soon as this command is selected, a new screen can be displayed representing in a substantially identical manner the preceding graphical interface, more particularly, the four icons of the main commands (the quarter disks of the previous commands). In other words, the basic screen presents the four icons of the main commands (blood glucose, meal, activity, type of day) and a "history" command which makes it possible to display a new screen comprising the same icons as those of the main commands. These new icons make it possible to access the history of each main command.

Figure 6:
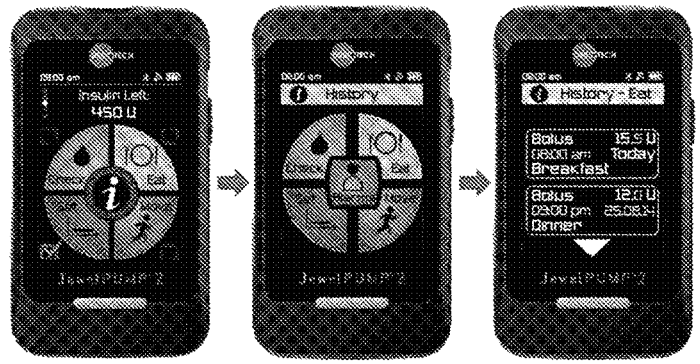

An illustration of this succession of screens is disclosed by FIG. 6. This figure shows three screens which follow one another, the first is the main (or basic) screen, the second is the history screen showing the same icons as the preceding screen and the third screen displays the history of the meal command (after selection of the meal command in the history). This screen lists the different types of meals taken, the time and date they were informed and the quantity of insulin injected.

At the center of the "history" screen there can be another icon such as, for example, a "return" command or an "alarm" command which will display, if the user selects this command, the history of the alarms.

The patient graphical interface also allows other successions of screens comprising icons having similar graphic characteristics between a first screen and a second screen. For example:

if the user selects the "meal" command of the basic screen (FIG. 3.1) then a second screen (FIG. 3.2) will be able to be displayed presenting icons having the same form as the icons of the commands of the basic screen. That is to say, here, four quarter disks.

If the user selects the "activity" command of the basic screen (FIG. 3.1) then a second screen and optionally a third screen (FIGS. 3.6 and 3.7) will be able to be displayed showing icons having the same form as the icons of the commands of the basic screen. That is to say, here, four quarter disks.

If the user selects the "type of day" command of the basic screen (FIG. 3.1) then a second screen (FIG. 3.9) will be able to be displayed showing icons having the same form as the icons of the commands of the basic screen. That is to say, here, four quarter disks.

The color code of the main command can be used as a distinctive sign of the commands. Thus, the background color of the icon (for example yellow) can be used by the other icons of the second screen or displayed in a specific zone such that the user recognizes the command previously selected. In other words, at least one distinctive sign of the command selected in the first screen is illustrated unequivocally by the second screen.

At the end of each command, the control device can display a summary screen and/or request a confirmation code (PIN code for example).

Other Examples of Interfaces

The system is particularly suited to type 2 diabetics because it requires only little knowledge of the disease on the part of the patient and also by virtue of its ease of use. However, it may be advantageous to use this system for a type 1 diabetic, particularly when the user (for example the patient or a parent of the patient) is in a phase of learning how to treat his or her disease. Thus, the system can evolve with the patient. In a first stage, the system will propose only very basic functionalities then the prescriber will be able to add (or remove) over time (after several weeks, months and years, or according to the age of the patient) other functionalities. The functionalities presented hereinbelow may also be available only to a responsible person (that is to say not accessible to the patient but, for example, to a caregiver or a parent).

In FIG. 9.1, this functionality allows a more experienced user to control different types of bolus (single, extended or dual).

In FIGS. 9.1 and 9.2, the screen proposes additional information in addition to three possible control instructions. This additional information can be the last blood glucose measurement of the patient, it could also be the last bolus command or the need (or the prompting) to perform a new measurement of the blood glucose (for example if the last measurement is too old).

In FIG. 9.3, the screen allows the user to activate or deactivate the correction(s) proposed by the control device according to the last blood glucose measurement and/or according to the remaining quantity of insulin active in the body of the patient, that is to say the insulin which has been injected into the patient and which will (in the near future) have an action on the blood glucose of the patient. On this screen, the patient has ordered a quantity of 10 U of insulin, the device proposes adding 5.5 U thereof to correct the blood glucose and to remove 3.5 U therefrom to take account of the quantity of insulin still present in his or her body.

In FIG. 10, the device allows the user to order a dual bolus. This is the infusion of a bolus in two successive steps. Firstly, the delivery device will inject a first quantity of insulin during a first period, then, during a second period, the device will inject a second quantity of insulin. The control device thus proposes a succession of screens making it possible to control a dual bolus. In a first screen, the user selects the "dual bolus" control instruction then another screen allows the user to decide on the distribution of the quantity of insulin to be injected during the first and second periods. This can be a distribution bar whereby the user can define this distribution by moving it to the right or to the left. The screen can inform the user of this distribution either in units or as a percentage per period, the calculation can be performed automatically when the user moves the distribution bar. Another screen allows the user to define at least the duration of the second period. A last screen summarizes all of this control instruction in particular the total quantity of insulin ordered for this control instruction.

Figure 11:
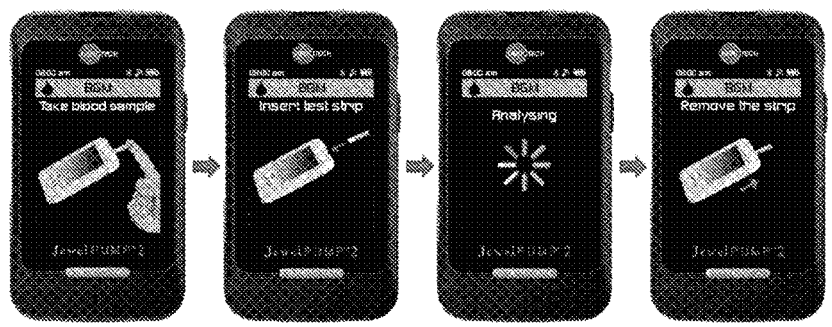
Figure 12:

FIGS. 11 and 12 show how a user can be guided during a procedure. For example, FIG. 11 presents a succession of screens explaining to the user the steps necessary to perform a blood glucose measurement using a BGM. This BGM can be a function of the control device. FIG. 12 explains how to fill a tank of the delivery device. These screens may contain text, numerals, symbols, fixed and/or moving graphical illustrations, a video. Sound information can also provide more comprehensive information or orally describe the procedure. This is a genuine advantage for unaccustomed people and that makes it possible to teach the user the procedure to be carried out.

Figure 13:

The images of FIG. 13 present screens comprising additional information on the screen. In one embodiment, this is a box that is checked or not checked (or unchecked). For example:

if the box alongside the blood glucose input command ("CHECK") is checked that can mean that the last blood glucose measurement has been performed, measured or input within a certain time period. Also, this measurement may even be valid and may be used for the correction in the case of a bolus command.

If the box alongside the basal command ("SET") is checked, that can mean that a basal profile or that a basic rate is currently being delivered. If it is unchecked, no basal injection is performed by the delivery device.

If the box alongside the bolus command ("EAT") is checked, that can mean that the delivery device is currently delivering a recently ordered bolus. This may also mean that:

insulin still active is present in the body of the patient, this box would therefore be a function of a mathematical model which calculates the IOB (Insulin on Board) over time due to a bolus injection.

The patient can now order a bolus. Thus, a prescriber will have previously designated time bands during which the patient or other user can order a bolus command. This activation of the bolus command can also be illustrated by a colored key which is grayed out when the command is deactivated.

If the box alongside the activity command ("MOVE") is checked, that can mean that the system takes account of the fact that the patient at this moment performs a temporary physical activity.

It will also be noted that the headings of the commands have no medical connotation, so the control device does not remind the patient that he or she is sick, the patient lives better with his or her sickness and is thus more cooperative. In other words, the control device does not return a negative and restrictive image of the medical treatment, it simply allows the user to enter data which are linked to the activity of the patient (taking of a meal, lifestyle, physical activity, etc).

The system is adapted to increase the awareness of or train a user to live better with a sickness such as diabetes. In effect, using its basic screen, the patient instantaneously sees the four correct modes of conduct:

regularly measure the blood glucose of the patient
order a bolus to offset the input of carbohydrates in a meal
adapt his or her basal profile to his or her lifestyle
reduce his or her insulin input during a physical activity. The activity key also makes it possible to prompt a patient to perform a physical activity that is temporary but to do so regularly.

The system thus comprises a teaching function. Furthermore, the system can comprise a reminder system for reminding the patient to inform the system of the taking of a meal or not, the measurement of blood glucose, etc. The succession of screens and in particular that of the bolus command can allow the user to learn to estimate his or her insulin needs according to the type of meal and, optionally, the relative quantity (relative to the quantity of a standard meal of the patient) ingested during this meal.

Examples of Embodiments and of Use

The invention describes a control interface for controlling a medical treatment system which comprises preprogrammed control instructions. The control interface comprises:
  a display device,
  an input device for receiving at least one user input,
  a processor configured to process control instructions.

The input device is suitable for receiving a datum linked to the activity of the patient and informing the system of this datum. The processor is suitable for suggesting, through the display device, a control instruction that can take into account one or more preprogrammed control instructions, the activity of the patient and/or at least one other datum input by the user or determined by the system.

Another datum input by the user can be: a type of meal, the quantity of said meal, a level of effort linked to a physical activity, a duration of physical activity performed by the patient, a state of health, a blood glucose measurement, a day of the week, a time, a period or a type of day. Another datum determined by the system can be: a type of meal, data measured by a sensor suitable for recording the movements of the patient, a duration of physical activity performed by the patient, a state of health, a blood glucose measurement, a day of the week, a time, a period or a type of day.

According to one embodiment, the activity of the patient is the taking of a meal. Furthermore, the input device is suitable for informing of the type of meal and/or a quantity ingested by the patient. The type of meal can be a breakfast, a lunch or a dinner. A quantity ingested by the patient can be a relative quantity in relation to the quantity usually ingested by the patient. The interface can be adapted to suggest a type of meal according to a time band and/or the meal previously entered. In other words, the processor can take account of these data.

According to one embodiment, the activity of the patient is a temporary physical activity. Furthermore, the input device can be adapted to inform of the level of effort and/or the duration of the temporary activity performed by the patient.

According to one embodiment, the activity of the patient is the usual activity of the patient during a typical day. Furthermore, the input device can be adapted to inform of the current type of day of the patient.

The control instructions can be dependent on the date and/or the time of the current day. The control interface can be adapted to suggest a control instruction taking into account at least one control instruction previously executed. A communication means can make it possible to send data to a remote device in case of a compliance fault.

The processor can be adapted to send a reminder automatically to the user when the user has omitted to send a control instruction. The display device can be adapted to display a main menu allowing access to the main control instructions from a single screen. The input device can be adapted to receive at least one input from a prescriber allowing the parameterizing of at least one control instruction. The patient cannot have access to the parameterizing of the control instructions. The input device can be adapted to adjust the control instructions according to at least one given increment. This increment can be parameterized by the prescriber. The bolus increment can be a function of the time before or after the presumed time of delivery (i.e. meal) or of a sensitivity function of the patient according to the time of day.

The invention also describes a system for controlling the administration of a fluid to a patient, this system comprises:
  a fluid administration device configured to deliver a fluid to a patient,
  a control device designed to send delivery commands to the administration device.

The control device preferentially comprises input means and a display device suitable for offering together two distinct interfaces:
  a prescriber interface, and
  a patient interface.

The prescriber interface is designed to edit a delivery command suited to a given patient and to parameterize input means of the user interface whereas the patient interface is designed to send a delivery command to the administration device and/or to adjust a delivery command according to the activity of the patient and/or at least one other datum input by the patient or determined by the system. Some input means may only be able to be used via the prescriber interface. The input means of the user interface may be represented by virtual or physical buttons comprising icons, pictograms or specific symbols. Input means of the patient interface can be designed to increase or reduce the quantity delivered by predetermined increment. The increments can be variable as a function of time and/or edited via the prescriber interface. The patient interface can be designed to suggest a delivery command as a function of time and of data pre-parameterized via the prescriber interface. Furthermore, at least one of the interfaces can be adapted to be accessible only for the user of a password or via a specific unlocking means. For example, the prescriber interface cannot be accessible to the patient. The adjustment of a delivery command can be temporary. A delivery command can be defined over a certain duration pre-parameterized via the prescriber interface. A delivery command can be defined over a certain duration itself defined via the user interface by increments determined via the prescriber interface. A delivery command can be adjusted according to the suggestion of the control device following the input of a physiological datum of the patient. A processor can be adapted to monitor the compliance of the treatment. The system can further comprise communication means for exchanging data with a remote device, for example for monitoring the compliance of the treatment. The system can comprise an internal clock suitable for informing the system of the current date and/or time.

The invention also describes a method for controlling a medicine delivery device using a control device comprising a display device, an input device, a control interface, a processor. The method comprises the following steps:
  the establishment of control instruction suggestions taking into account one or more preprogrammed control instructions, the activity of the patient and/or at least one other datum input by the user or determined by the control device;
  the display of at least one suggestion on the display device;
  the activation via the input device by the patient of at least one suggested control instruction.

The method can further comprise at least one of the following additional steps:
- modification of the control instruction by predefined increments, said modification being able to be performed by the patient;
- modification of the control instructions preprogrammed by a prescriber via the input device;
- modification of the increments by a prescriber via the input device.

The invention also describes a method for treating the diabetes of a patient using a treatment system which comprises a memory, an input device, a display device all linked to a processor. The system can be adapted to execute at least one pre-parameterized control instruction, the method comprises the following steps:
- informing the system as to the activity of the patient via the input device;
- suggesting a control instruction according to pre-parameterized data, the activity of the patient and at least one other datum input by the user or determined by the system;
- validating the suggestion;
- executing the control instruction.

The method can optionally comprise at least one of the following steps:
- informing the system as to the type of meal ingested by the patient;
- informing the system as to the quantity ingested by the patient, for example the relative quantity in relation to the quantity usually ingested by the patient;
- informing the system as to the level of effort of the temporary activity performed by the patient;
- informing the system as to the duration of the temporary activity performed by the patient;
- pre-parameterizing at least one control instruction and saving it in the memory;
- adjusting the control instruction;
- adjusting the control instruction according to pre-parameterized increment;
- pre-parameterizing at least one increment;
- receiving measurements of the blood glucose of the patient and adjusting the control instruction according to the blood glucose measurement.

The pre-parameterizing can be performed by a specific user. The patient cannot pre-parameterize the control instructions.

The invention also describes a learning method for a patient for his or her treatment for diabetes, said method being able to comprise the following steps:
- use of a control interface as described in one of the preceding embodiments;
- informing of the activity of the patient;
- suggestion by the system and display of the control instruction suited to the need of the patient according to pre-parameterized data and the activity of the patient;
- validation of the suggested control instruction.

The invention also describes a method for recommending a quantity of insulin to be injected before, during or after a meal, said method can comprise the following steps:
- use of a control interface as described in one of the preceding embodiments;
- informing of the type of meal ingested or which will be ingested;
- optionally, informing of the quantity ingested relative to the quantity of a standard meal of the patient;
- computation by the processor of the quantity of insulin suited to the need of the patient according to the information given;
- display of the recommended quantity of insulin.

The invention also describes a method for recommending the adjustment of a quantity of insulin to be injected before, during or after a temporary physical activity performed by a patient, said method can comprise the following steps:
- use of a control interface as described in one of the preceding embodiments;
- informing of the level of effort of the patient during said physical activity and/or of the duration of said physical activity;
- computation by the processor of the quantity of insulin suited to the need of the patient according to the information given;
- display of the recommended quantity of insulin.

The invention claimed is:

1. A system for suggesting a fluid dose for a patient via a graphical user interface and for delivering the fluid dose to the patient, the system comprising:
a fluid administration device configured to deliver the fluid dose to the patient; and
a control device configured to provide a delivery command to the fluid administration device, the control device including a processor, an input device, and a display device, the processor configured to generate the graphical user interface on the display device, the control device further configured to
display a first list of elements, each element of the first list of elements representing a meal type taken or to be taken by the patient,
receive a first user input from a user of the control device selecting the meal type from the first list of elements,
display a graphical element representing a quantity of the selected meal type, wherein the quantity of the selected meal type is a quantity relative to a quantity usually taken by the patient,
receive a second user input from a user of the control device specifying the quantity of the selected meal type,
display a suggested delivery command for the patient, the suggested delivery command including at least one of a fluid delivery flow rate, a fluid delivery quantity, and a fluid delivery duration to be performed by the fluid administration device, the suggested delivery command determined based on (i) the received first user input and (ii) the received second user input,
display a command for increasing and decreasing a value of the suggested delivery command by predefined increments while simultaneously displaying the suggested delivery command, the predefined increments defined based on the received second user input,
receive a third user input from the user of the control device modifying the value of the suggested delivery command by increasing or decreasing the value by the predefined increments,
adjust the suggested delivery command according to the modified value while simultaneously displaying the adjusted delivery command,
display a validation command permitting a validation of the adjusted delivery command by the user,
accept the validation command by a fourth user input to validate the adjusted delivery command, and provide the validated delivery command to the fluid administration device, wherein the fluid administration device is configured to deliver the fluid dose to the patient according to the validated delivery command.

2. The system as claimed in claim 1, wherein the suggested delivery command for the patient is further determined based on (iii) preprogrammed control device delivery commands.

3. The system as claimed in claim 1, wherein the first list of elements is represented by virtual buttons including at least one of icons, pictograms, and specific symbols.

4. The system as claimed in claim 1, wherein the graphical element representing a quantity of the selected type of meal is represented by virtual buttons including at least one of icons, pictograms, text and specific symbols.

5. The system as claimed in claim 1, wherein the meal type includes a breakfast, lunch, dinner, supper or snack.

6. The system as claimed in claim 1, wherein the processor is further configured to graphically suggest a selection of an element for the first list depending on a current time, a current day or a previous selection of the first list of elements.

7. The system as claimed in claim 6, wherein the graphically suggesting highlights one element of at least one of the first list of elements as the selection.

8. The system as claimed in claim 1, wherein the predefined increments are variable as a function of time.

9. The system as claimed in claim 1, wherein the graphical user interface is configured to suggest the suggested delivery command as a function of time and data pre-parameterized via a prescriber interface.

10. The system as claimed in claim 9, wherein the prescriber interface is accessible via at least one of a password and a specific unlocking device.

11. The system as claimed in claim 1, wherein the processor is further configured to control the graphical user interface to permit a selection of an element of the first list depending on the type of meal previously taken or selected by the user.

12. A method for suggesting a fluid dose for a patient via a graphical user interface of a control device and for delivering the fluid dose to the patient with a fluid administration device, the method comprising the steps of:

first displaying a first list of elements on the graphical user interface, each element of the first list of elements representing a meal type taken or to be taken by the patient;

first receiving a first user input from a user of the control device, the first user input selecting the meal type from the first list of elements;

second displaying a graphical element on the graphical user interface representing a quantity of the selected meal type;

second receiving a second user input from the user of the control device specifying the quantity of the selected type of meal;

third displaying a suggested delivery command for the patient on the graphical user interface, the suggested delivery command including a fluid delivery flow rate, a fluid delivery quantity, or a fluid delivery duration to be performed by the fluid administration device, the suggested delivery command determined based on (i) the received first user input and (ii) the received second user input;

fourth displaying a command on the graphical user interface for increasing and decreasing a value of the suggested delivery command by predefined increments while simultaneously displaying the suggested delivery command by the step of third displaying, the predefined increments defined based on the received second user input;

third receiving a third user input from the user of the control device modifying the value of the suggested delivery command by increasing or decreasing the value by the predefined increments;

adjusting the suggested delivery command according to the modified value while simultaneously displaying the adjusted delivery command;

fifth displaying a validation command on the graphical user interface, permitting a validation of the adjusted delivery command by the user;

accepting the validation command by a fourth user input to the control device to validate the adjusted delivery command;

providing the validated delivery command to the fluid administration device; and delivering the fluid dose to the patient by the fluid administration device according to the validated delivery command.

13. The method according to claim 12, wherein in the step of second displaying, the quantity taken by the patient being a relative quantity in relation to a quantity usually taken by the patient.

14. The method according to claim 12, wherein in the step of third displaying, the suggested delivery command for the patient is further determined based on (iii) preprogrammed control device delivery commands.

15. The method according to claim 12, wherein the first list of elements is represented by virtual buttons including at least one of icons, pictograms, and specific symbols.

16. The method according to claim 12, further comprising a step of:

graphically suggesting a selection of an element for the first list depending on a current time, a current day or a previous selection of the first list of elements.

17. The method according to claim 12, further comprising the step of:

permitting a selection of an element of the first list of the step of first displaying depending on the type of meal previously taken or selected by the user.

18. The method according to claim 12, wherein the step of third displaying determines the suggested delivery command as a function of time and data pre-parameterized via a prescriber interface.

19. A system for suggesting a fluid dose for a patient via a graphical user interface and for delivering the fluid dose to the patient, the system comprising:

a fluid administration device configured to deliver the fluid dose to the patient; and a control device configured to provide a delivery command to the fluid administration device, the control device including a processor, an input device, and a display device, the processor configured to generate the graphical user interface on the display device, the control device further configured to display a first list of elements, each element of the first list of elements representing a meal type taken or to be taken by the patient, receive a first user input from a user of the control device, selecting the meal type from the first list of elements, display a command on the graphical user interface for increasing or decreasing a pre-selected quantity of the selected type of meal taken or to be taken by the patient, receive a second user input from the user of the control device modifying the pre-selected quantity of the selected type of meal by increasing or decreasing the pre-selected quantity, determine a suggested delivery command to be performed by the fluid administration device, the suggested delivery command including at least one of a fluid delivery flow rate, a fluid delivery quantity, and a fluid delivery duration, based on (i) the received first user input and (ii) the received second user input, and simultaneously display the suggested delivery command, display a command on the graphical user interface for increasing and decreasing a value of the suggested delivery command by predefined increments while simultaneously displaying the suggested delivery command, the predefined increments defined based on the received second user input, receive a third user input from the user of the control device modifying the value of the suggested delivery command by increasing or decreasing the value by the predefined increments, adjust the suggested delivery command according to the modified value while simultaneously displaying the adjusted delivery command, display a validation command permitting a validation of the adjusted delivery command by the user, accept the validation command by a fourth user input to validate the adjusted delivery command, and provide the validated delivery command to the fluid administration device, wherein the fluid administration device is configured to deliver the fluid dose to the patient according to the validated delivery command.

20. The system as claimed in claim 19, wherein the predefined increments are variable as a function of time.

21. The system as claimed in claim 19, wherein the meal type includes a breakfast, lunch, dinner, supper or snack.

22. The system as claimed in claim 19, wherein the processor is further configured to graphically suggest a selection of an element for the first list of elements depending on a current time, a current day or a previous selection of the first list of elements.

23. The system as claimed in claim 22, wherein the graphically suggesting highlights one element of at least one of the first list of elements as the selection.

24. The system as claimed in claim 19, wherein the graphical user interface is configured to suggest the suggested delivery command as a function of time and data pre-parameterized via a prescriber interface.

* * * * *